Sept. 18, 1956
J. B. VOSTERS
FICUS PLANTS
Filed Nov. 1, 1955
Plant Pat. 1,519
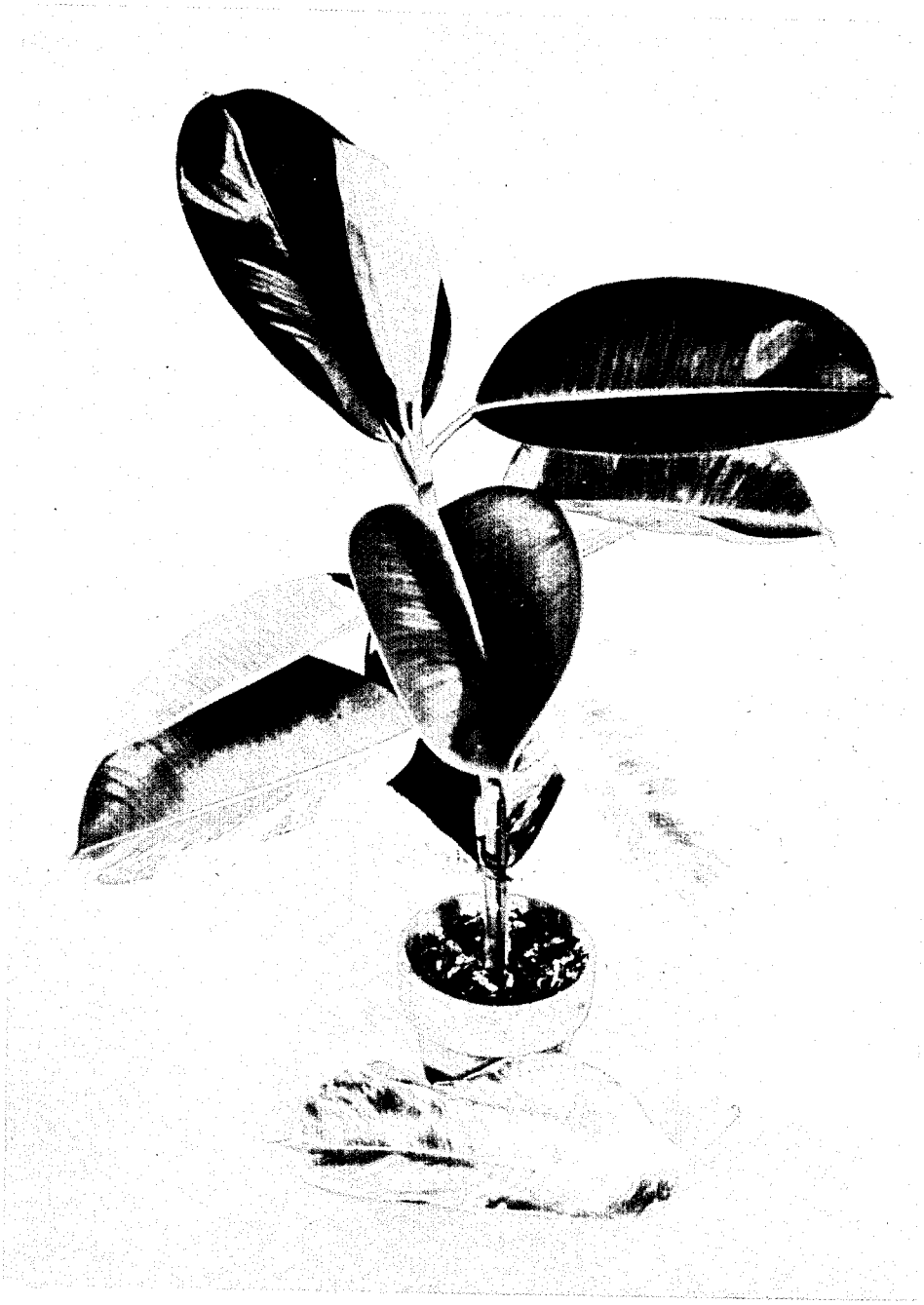
INVENTOR
James B. Vosters
By Orville M Kile
Plant Patent Agent United States Patent Office Plant Pat. 1,519

Patented Sept. 18, 1956

1,519

FICUS PLANTS

James B. Vosters, near Miami, Fla., assignor to Vosters Nurseries, Inc., Dade County, Fla.

Application November 1, 1955, Serial No. 544,389

1 Claim. (Cl. 47—59)

My present discovery relates to a new variety of Ficus belonging to the ornamental sub-family commonly known as "rubber plants." My new variety is a sport of *Ficus decora,* from which it is readily distinguishable by its variegated leaves and its more compact growth, that is, lesser space between leaf nodes.

This new variety was first noted by me in my nurseries at Cutler, Florida, as a sport of one of the many *Ficus decora* (not patented) plants I had growing there. After taking special precautions to protect it during an observation period, I reproduced it asexually both by air-layering and by cuttings. The distinguishing characteristics appear to be well established in the progeny.

The accompanying illustration shows a typical plant of this new variety at the age of approximately 6 months, also a fully matured leaf leaning against the flower pot. The yellow and mottled yellow and green effects are most notable on the lower and older leaves, since part of the greens gradually change to yellows as the leaf matures. The colors shown are as nearly true as the color photographer could make them, but greens and yellows are difficult to photograph and some allowance must be made. Some of the greens in the illustration should be a somewhat deeper shade, and the bluish tints seen on some of the upper leaves of the color photograph are not visible in the plant itself.

In the following description the color terms designated by plate numbers are from Ridgway's Color Standards and Nomenclature, but elsewhere ordinary dictionary color references are used.

*The plant.*—The general size of the plant and the leaves can be judged by the fact that the flower pot shown is six inches across the top. The plant illustrated is approximately 23 inches tall, measured from the surface of the dirt to the end of the top center leaf.

*The leaves.*—When fully matured, the leaves are 10 to 12 inches long and 7 to 7½ inches wide, with petioles 1¾ to 2 inches long. At the terminal end of each leaf there is a prominent sharp point turning downward. The midrib is very prominent and the texture of the leaf is very leathery.

The distance between nodes on the typical plant illustrated is about an inch, at a height of 9 inches above the ground—less than an inch upward from that point and somewhat more than an inch toward the base of the plant.

Leaves are arranged spirally around the central stem.

*Coloring.*—The newer leaves at the top of the plant are green to brownish-green with only a suggestion of yellow. The reverse side usually has a reddish tinge, particularly prominent on the midrib. This reddish color fades as the leaf matures.

On two-thirds-grown leaves the yellow may reach entirely around the margin of the leaf and toward the midrib to a depth of 1½ inches.

The mature leaves usually have a mottled appearance at least over a considerable portion of their surfaces, with various shades of yellow and green, the pattern extending out from the midrib along the laterals and on some leaves giving a marbled effect where the yellow shows through or displaces the green in an irregular pattern. On some leaves a dark green will cover the edge of the leaf to a depth of 1 to 2 inches for a quarter or more of the perimeter.

There is a great deal of variation between mature individual leaves on the same plant, some having much more yellow or mottled or marbled appearance than others. As the leaf fully ripens and shortly before dropping, it shows a brown, dead spot that gradually enlarges. There is a long period, however, between the time the leaf is fully variegated and colored and the time when the brown spot begins to show.

The darker greens referred to above are approximately Forest Green (Pl. XVII) and the lighter greens are Biscay Green to Courge Green (both Pl. XVII).

The yellows range from Massicot Yellow through Straw Yellow to Amber Yellow (all Plate XVI).

The variety of Ficus which my new variety most resembles is *Ficus decora* (unpatented). My new variety is readily distinguishable from *Ficus decora* by its variegated and mottled leaves. It is also a more compact plant because of the shorter distance between leaves or nodes.

Having thus disclosed my invention, I claim:

The new and distinct variety of Ficus plant substantially as herein shown and described, characterized particularly by its large variegated and mottled leaves of various shades of green and yellow, and by its compact form due to shorter distances between leaves or nodes.

No references cited.